US006969358B2

(12) United States Patent
Baltschun et al.

(10) Patent No.: US 6,969,358 B2
(45) Date of Patent: Nov. 29, 2005

(54) AUTOMATIC BIOPSY DEVICE FOR USE IN AN MRT

(75) Inventors: Horst Baltschun, Rülzheim (DE); Judith Bast, Wörth (DE); Holger Frenzel, Bruchsal (DE)

(73) Assignee: Forschungszentrum Karlsruhe GmbH, Karlsruhe (DE)

( * ) Notice: Subject to any disclaimer, the term of this patent is extended or adjusted under 35 U.S.C. 154(b) by 166 days.

(21) Appl. No.: 10/303,099

(22) Filed: Nov. 23, 2002

(65) Prior Publication Data

US 2003/0073929 A1   Apr. 17, 2003

Related U.S. Application Data

(63) Continuation-in-part of application No. PCT/EP01/08957, filed on Aug. 2, 2001.

(30) Foreign Application Priority Data

Aug. 30, 2000 (DE) .............................. 100 42 519

(51) Int. Cl.[7] ............................................. A61B 10/00
(52) U.S. Cl. ...................... 600/567; 600/564; 606/167
(58) Field of Search ............................. 600/564–568; 606/184, 185, 167; 604/114.01

(56) References Cited

U.S. PATENT DOCUMENTS

| 4,958,625 | A | * | 9/1990 | Bates et al. ................. 600/567 |
| 5,007,903 | A | * | 4/1991 | Ellard ......................... 604/195 |
| 5,335,672 | A | | 8/1994 | Bennett |
| 5,476,101 | A | | 12/1995 | Schramm et al. |
| 5,617,874 | A | | 4/1997 | Baran |
| 5,782,764 | A | | 7/1998 | Werne |
| 5,868,785 | A | * | 2/1999 | Tal et al. .................... 606/207 |
| 5,951,489 | A | | 9/1999 | Bauer |
| 5,993,399 | A | | 11/1999 | Pruitt et al. |
| 6,120,463 | A | * | 9/2000 | Bauer ......................... 600/567 |
| 6,254,620 | B1 | * | 7/2001 | Koh et al. ................... 606/167 |

FOREIGN PATENT DOCUMENTS

WO      WO 98/33435      6/1998

* cited by examiner

Primary Examiner—Max F. Hindenburg
Assistant Examiner—Jonathan Foreman
(74) Attorney, Agent, or Firm—Klaus J. Bach

(57) ABSTRACT

In an automatic biopsy device comprising a housing in which a biopsy needle is axially movably supported by a needle support structure and a cannula extending around the needle is axially movably supported by a cannula support structure, and first and second spring force storage structures are provided for biasing the biopsy needle and the cannula, respectively, toward an extended position and the biopsy needle and cannula support structures are held in a retracted position by respective first and second releasable locking means, releasing means are provided for manually releasing the first locking means to permit the needle to be propelled by the first spring force storage structure and to release the second locking structure by releasing means of the needle support structure to permit the cannula to be propelled by the second spring force storage structure, the biopsy needle and cannula and also the spring force storage structures consisting of a non-magnetizable electrically non-conductive material.

2 Claims, 7 Drawing Sheets

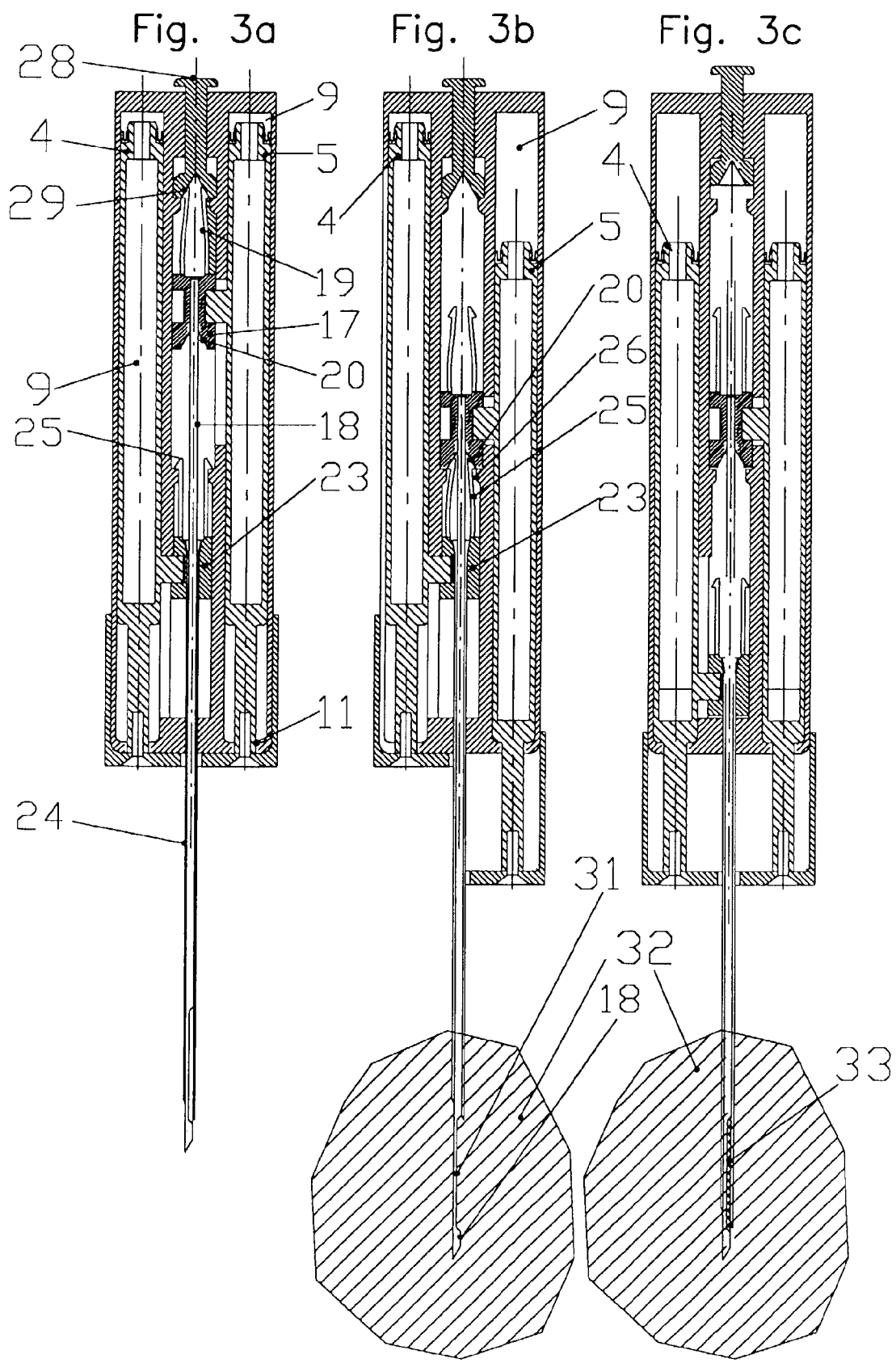

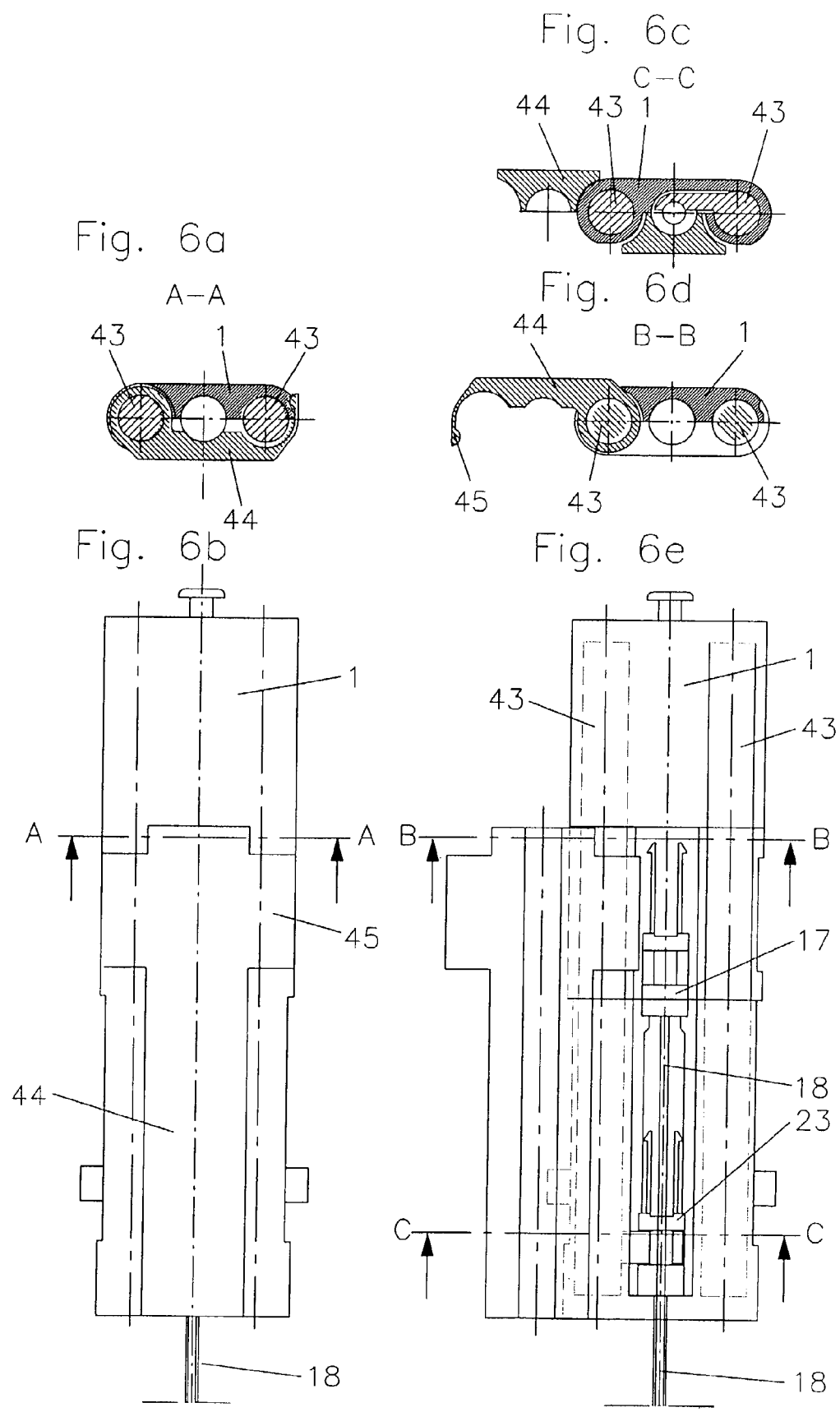

US 6,969,358 B2

AUTOMATIC BIOPSY DEVICE FOR USE IN AN MRT

This is a Continuation-In-Part application of international application PCT/EP01/08957 filed Aug. 2, 2001, and claiming the priority of German application 100 42 519.4 filed Aug. 3, 2000.

BACKGROUND OF THE INVENTION

The invention resides in a biopsy device for the removal of soft tissue samples from a living organism including a housing supporting a biopsy needle with recesses in its sides near the tip of the needle, a cannula which is axially movably disposed on the needle, a spring for moving the needle forwardly and a spring for moving the cannula forwardly.

In human and veterinary medicine, a targeted removal of soft tissue samples from the living organisms, called biopsy, is a solid part of the diagnosis in connection with numerous health problems. Often, only the examination of a tissue sample permits a safe diagnosis. Whereas a biopsy is performed usually on body parts which are accessible from the outside by surgical instruments, endoscopic procedures must be used for biopsies on internal body parts using for example a biopsy needle. The biopsy needle, which has a recess at its side near its tip, is inserted into the tissue to be examined so that the tissue enters the recess. Then a cannula is moved forwardly over the recess toward the needle tip whereby the tissue in the recess is severed and removed with the needle for examination.

There are three different types of biopsy devices. In manual biopsy devices, the needle is normally inserted and the cannula is manually moved forwardly. In semiautomatic biopsy devices, the needle is manually inserted, but the cannula is moved at high speed forwardly over the recess of the biopsy needle by the release of a compressed spring. Automatic biopsy devices include generally two spring force storage structures, one for the rapid forward movement of the biopsy needle into the predetermined target area and the other for the immediately following rapid forward movement of the cannula.

WO96/39941 discloses an automatic biopsy device which comprises a housing with a biopsy needle and a cannula supported therein so as to be axially movably disposed on the biopsy needle. It also includes for each a spring structure with a metal spring for a spring force driven forward movement of the biopsy needle and the cannula. For the automatic operation, first both springs are manually compressed or tensioned, whereby two guided members, on which the biopsy needle and the cannula are mounted, are retracted to an end position in which they are compressed or tensioned. Two guided members on which the biopsy needle and the cannula are mounted are retracted thereby to an end position where they are held by a simple locking mechanism disposed eccentrically with respect to the cannula and the biopsy needle. After the biopsy device is properly positioned, the locking mechanism for the biopsy needle is released whereby the needle is propelled by spring force toward the target area. Shortly before reaching the target area, the movement of the biopsy needle releases in the housing the locking mechanism for the cannula resulting in a spring force operated advance of the cannula. However, the biopsy device includes several metallic components, which are for example springs consisting of spring steel. This causes in the MRT picture distortions (artifacts) Steel springs are consequently not very suitable for use with MRT.

The biopsy needle with the cannula is provided in the form of a replacement unit in the housing with the two spring force storage structures.

However, if during an MRT examination a carcinoma is detected and if based on the image, a tissue sample is to be taken in the MRT, the biopsy device and the manipulator must be of such a design that no artifacts occur.

It is the object of the invention to provide a biopsy device with a spring force storage arrangement so that it is suitable for an image-based operation with an MRT in which strong magnetic fields (>1 Tesla) are present. Furthermore, the kinematics of the biopsy device should be improved so as to facilitate the replacement of the biopsy needles and cannulas and to improve generally the operation of the device.

SUMMARY OF THE INVENTION

In an automatic biopsy device comprising a housing in which a biopsy needle is axially movably supported by a needle support structure and a cannula extending around the needle is axially movably supported by a cannula support structure and first and second spring force storage structures are provided for biasing the biopsy needle and the cannula, respectively, toward an extended position and the biopsy needle and cannula support structures are held in a retracted position by respective first and second releasable locking means, releasing means are provided for manually releasing the first locking means to permit the needle to be propelled by the first spring force storage structure to release the second locking structure by releasing means of the needle support structure to permit the cannula to be propelled by the second spring force storage structure, the biopsy needle and cannula and also the spring force storage structures consisting of a non-magnetic electrically non-conductive material.

The invention will be described in greater detail below on the basis of the accompanying drawings.

BRIEF DESCRIPTION OF THE DRAWINGS

FIG. 6a to FIG. 6e show, for the embodiment according to FIG. 5, a housing structure which can be opened to provide access to the interior.

DESCRIPTION OF PREFERRED EMBODIMENTS

Figure 1:
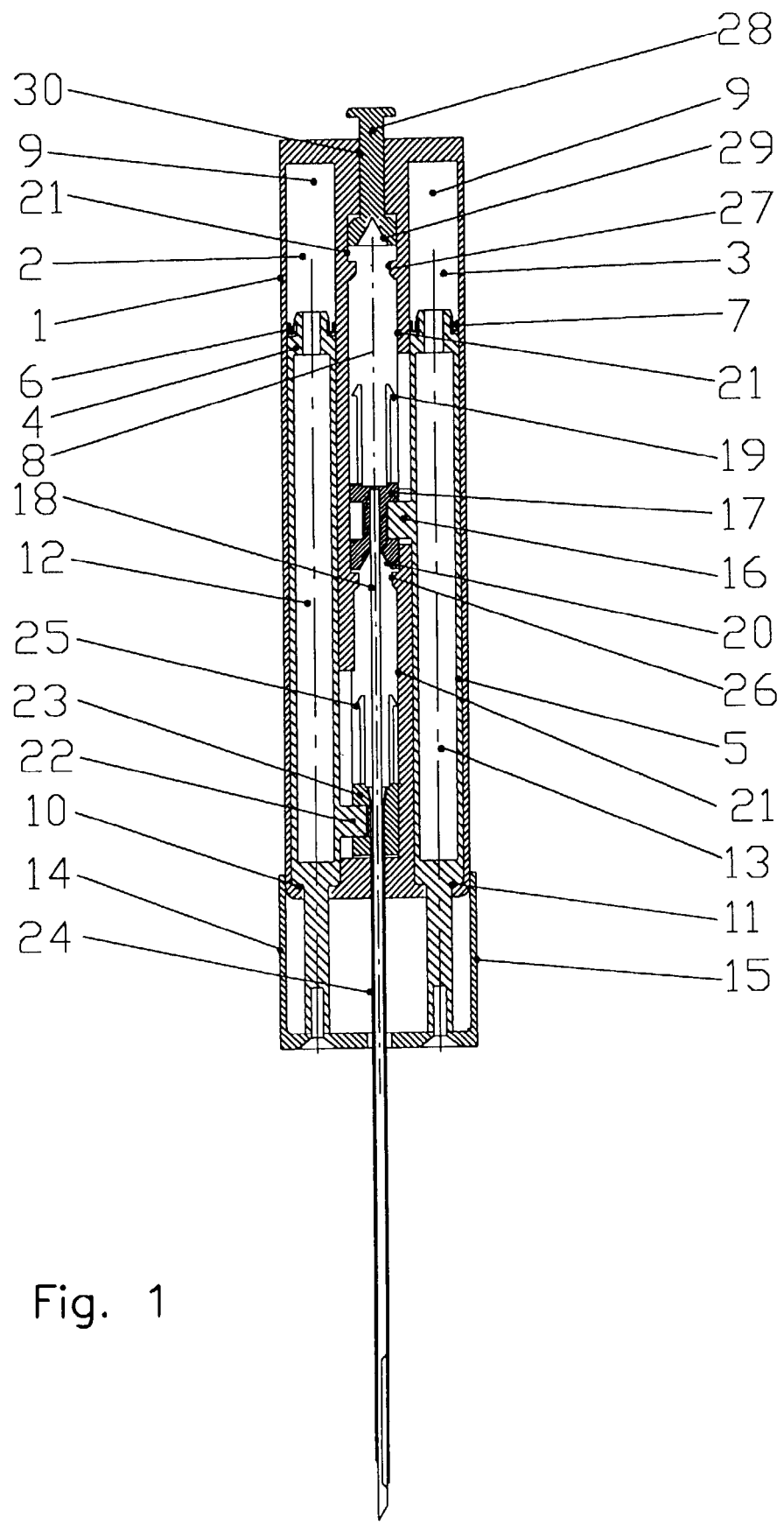
FIG. 1 is a cross-sectional view of a first embodiment of the invention including two fluid spring storage structures.

FIG. 1 shows a first embodiment of the biopsy device in a rest position that is in a position in which the springs are relaxed. It includes a housing 1 with two spring force storing structures comprising two bores 2 and 3 each including a piston 4, 5 with seals 6 and 7. The two bores 2 and 3 may be blind bores forming cylinder chambers. The bores 2, 3 include above the pistons 4 and 5 a gas which may be compressed to bias the pistons 4, 5 onto the seats 10 and 11 of the housing 1. The bores 12 and 13 in the pistons 4 and 5 are in communication with the cylinder chambers 2, 3 of the housing and commonly form an enlarged storage volume for the pressure medium 9. With the relatively large pressure fluid volume, the volume change caused by a movement of the piston is relatively small so that the pressure gradient during movement of a piston 4, 5 is also relatively small. The pistons 4 and 5 extend through the housing 1 and beyond the seats 10 and 11 and are each connected to a respective cap 14 and 15 so as to be movable therewith.

The piston 5 is provided with a projection 16, which extends into a circumferential groove of a coupling member 17 having an axis coinciding with the axis of symmetry 8 of the device. The coupling member 17 firmly engages the biopsy needle 18 and is axially movably supported in the central bore 21. At the end of the coupling member 17 opposite the biopsy needle 18, there are at least two resilient webs 19, which are provided at their upper ends with engagement hooks. At its end adjacent the biopsy needle 18, the coupling member 17 is provided with an inwardly directed conical area 20, which opens toward the biopsy needle 18.

In a similar way, a projection 22, which is connected to the piston 4, extends into a circumferential groove formed in the rotationally symmetrical coupling member 23, which serves as a carrier for the cannula 24 and to which the cannula 24 is firmly connected. Also, the coupling member 23 is axially movably supported in the bore 21. At the end of the coupling member 23 remote from the cannula, the coupling member 23 carries at least two resilient webs 25, which are provided at their free ends with engagement hooks.

As shown in FIG. 1, the biopsy needle 18 is inserted into the cannula 24 from the coupling member end thereof and is slidably supported in the cannula with little or no play.

The two coupling members 17 and 23, which are arranged in axial alignment one behind the other in the bore 21 and which are firmly connected to the biopsy needle 18 and, respectively, the cannula 24, ensure that the biopsy needle 18 as well as the cannula 24 are guided accurately along the axis of symmetry 8 without any other guide elements.

In the center part of the bore 21 between the two coupling members 17 and 23, a circumferential shoulder 26 is provided. Another circumferential shoulder 27 is at the upper end of the bore 21. The shoulders 26 and 27 serve as engagement ledges for the locking hooks of the engagement webs 19 and, respectively, 25, when they are in their retracted end positions in which the spring force storage devices are tensioned. The engagement webs 19 and 25 of the coupling members 17 and 23 are distributed around the circumference of the respective coupling members and the axis of symmetry 8 so that the coupling members 17 and 23 are supported in alignment with the axis of symmetry 8 and are not subject to cogging. Since the projections 16 and 22 extend relatively far into the grooves of the respective coupling members 17 and 23 preferably in the form of a fork, the engagement forces are advantageously distributed at opposite sides of the axis of symmetry 8, thereby avoiding the transmission of moments to the needle and, respectively, the cannula. Cogging of the coupling members 17 and 23 in the bore 21 is therefore very unlikely.

At the upper end of the housing, an actuating pin 28 is axially movably supported in an end bore 30 of the housing 1 for initiating the biopsy procedure. At its front end, the actuating pin 28 has a conical end surface 29, which is disposed in the bore 21 for unlocking the elastic webs 19 from the shoulder 27.

Figure 2A:
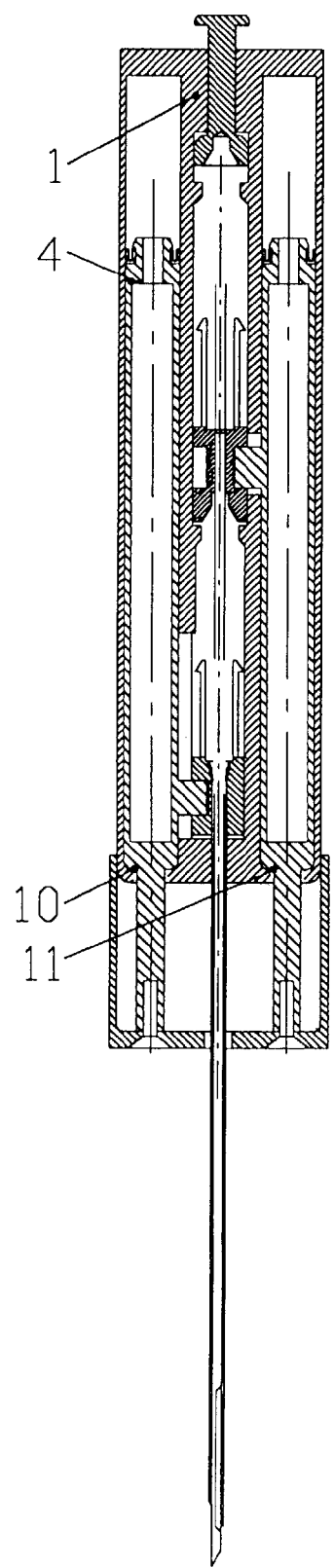
FIGS. 2a to 2c show the charging procedure of the biopsy device shown in FIG. 1, FIG. 3a to FIG. 3c show the needle and cannula insertion procedure with the device according to FIG. 1.
Figure 2B:
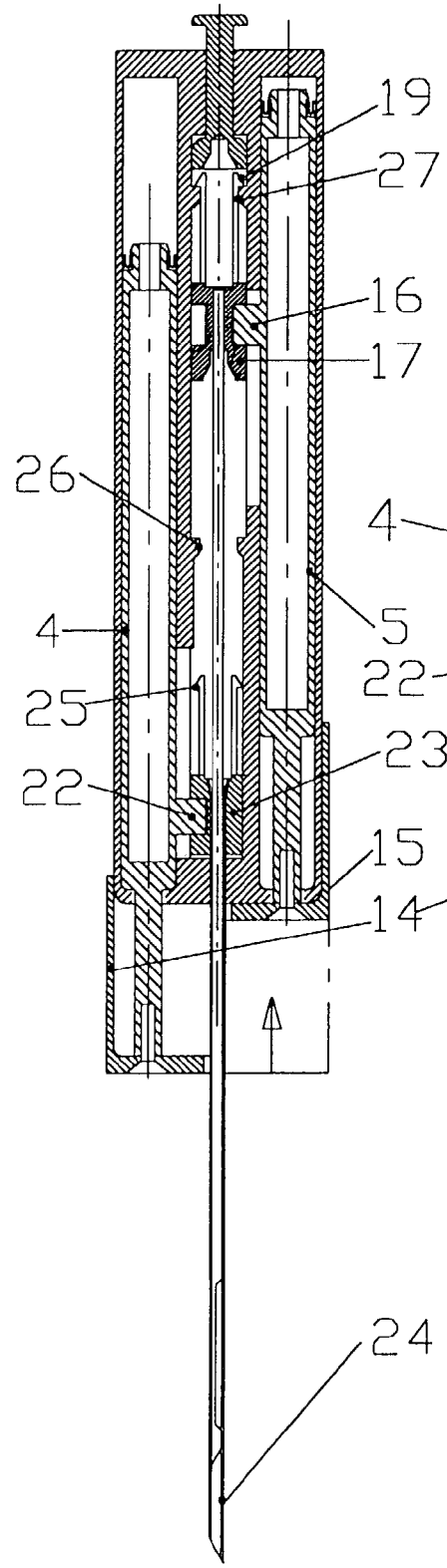
Figure 2C:
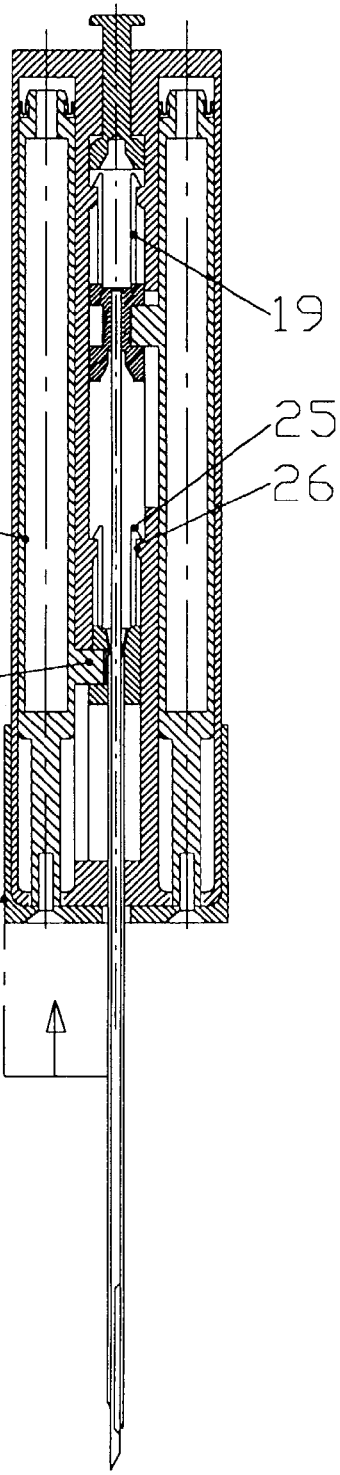

FIGS. 2a to 2c show the tensioning procedure of the biopsy device according to the first embodiment. FIG. 2a shows the biopsy device in the rest position, in which both spring force storage structures are released, that is, the two pistons 4 and 5 are seated on the stops 10 and 11 engaging them with a force according to the pre-pressurized pressure medium 9. (See also FIG. 1). In the following step as shown in FIG. 2b, the piston 5 is pushed by hand via the cap 15 into the bore 3 of the housing 1 whereby the pressure medium 9 is further compressed. Concurrently, with the piston 5, the coupling member 17 with the biopsy needle 18 is retracted until the locking hooks at the ends of the webs 19 engage the shoulder 27. Subsequently, or at the same time, the cannula 24 with the coupling member 23 and the piston 4 are retracted via the cap 14 against the pressure of the pressure medium 9 in the cylinder bore 2 until the locking hooks at the free ends of the webs 25 engage the shoulder 26 (FIG. 2c). Both spring force storage structures are now under tension. The biopsy device is now ready for use.

FIGS. 3a to 3c illustrate the insertion procedure for taking a tissue sample. The pistons 4 and 5 are at the beginning pressurized by the pressure medium 9. The locking hooks of the webs 25 and 19 of the coupling members 17 and 23 hold the biopsy needle 18 and the cannula 24 in the retracted position. Upon manual insertion of the actuating pin 28 into the housing 1, the elastic webs 19 of the coupling member 17 are pushed together inwardly by the conical end surface 29 so that, finally, the locking hooks are pushed off the shoulder 27 and the coupling member is released. Driven by the pressure medium, the biopsy needle 18 then is rapidly propelled forwardly into a patients tissue of which a sample is to be taken until the piston abuts the stop 11. Shortly before this instant the conical surface area 20 of the coupling member 17 engages the webs 25, which are thereby pushed toward each other so that the locking hooks of the webs 25 are pushed off the shoulder 26, whereby the coupling member 23 is released (FIG. 3b) so that the pressurized piston 4 can impel the cannula 21 over and toward the front of the biopsy needle 18. The forward movement of the cannula 24 is limited by the seating of the piston 4 on the stop 10 (FIG. 3c). Because of the high speed of the cannula 24, the tissue 32 present in the recess 31 of the biopsy needle 18 is cut off and the cannula 24 encloses the tissue sample 33. The biopsy device is now in its rest position and can be removed from the tissue for an examination of the tissue sample collected in the needle recess.

For the removal of the tissue sample 33, the cannula 24 is manually pulled back by pushing back the cap 14, whereby the recess 31 is exposed and the tissue sample 33 can be removed from the recess of the needle.

Figure 4:
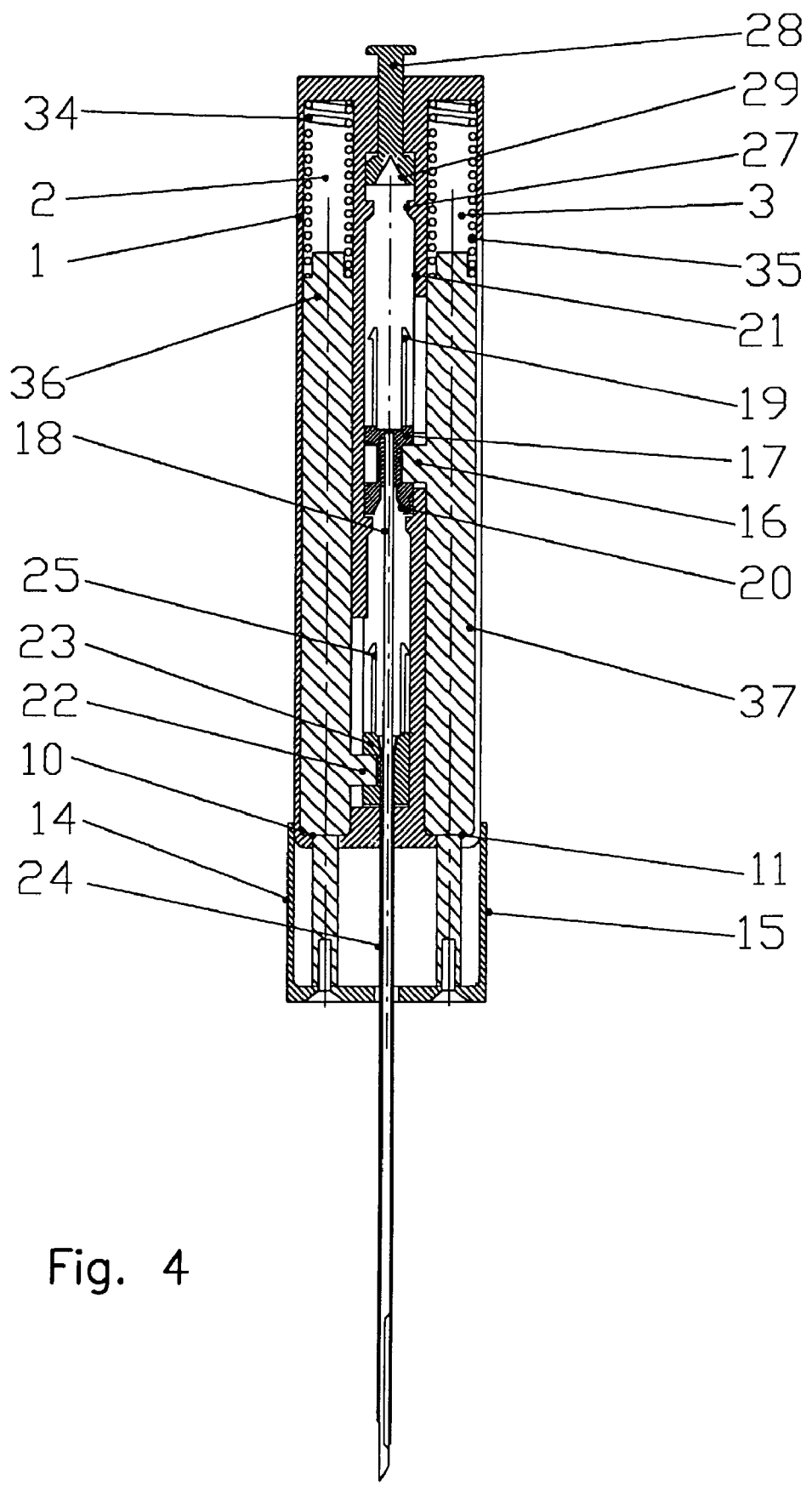
FIG. 4 is a sectional view of a second embodiment of the biopsy device using two spiral spring force storage structures.

The biopsy device of the second embodiment is shown in FIG. 4 in a rest position. It is different from the embodiment described above in that it is equipped, instead of a pressure medium 9, with compression springs 34 and 35, which act on the pistons 36 and 37. The operation of the device shown in FIG. 4, particularly the charging and release procedure according to FIGS. 2a to 2c and 3a to 3c, are the same as described for the embodiment of FIG. 1.

Figure 5:
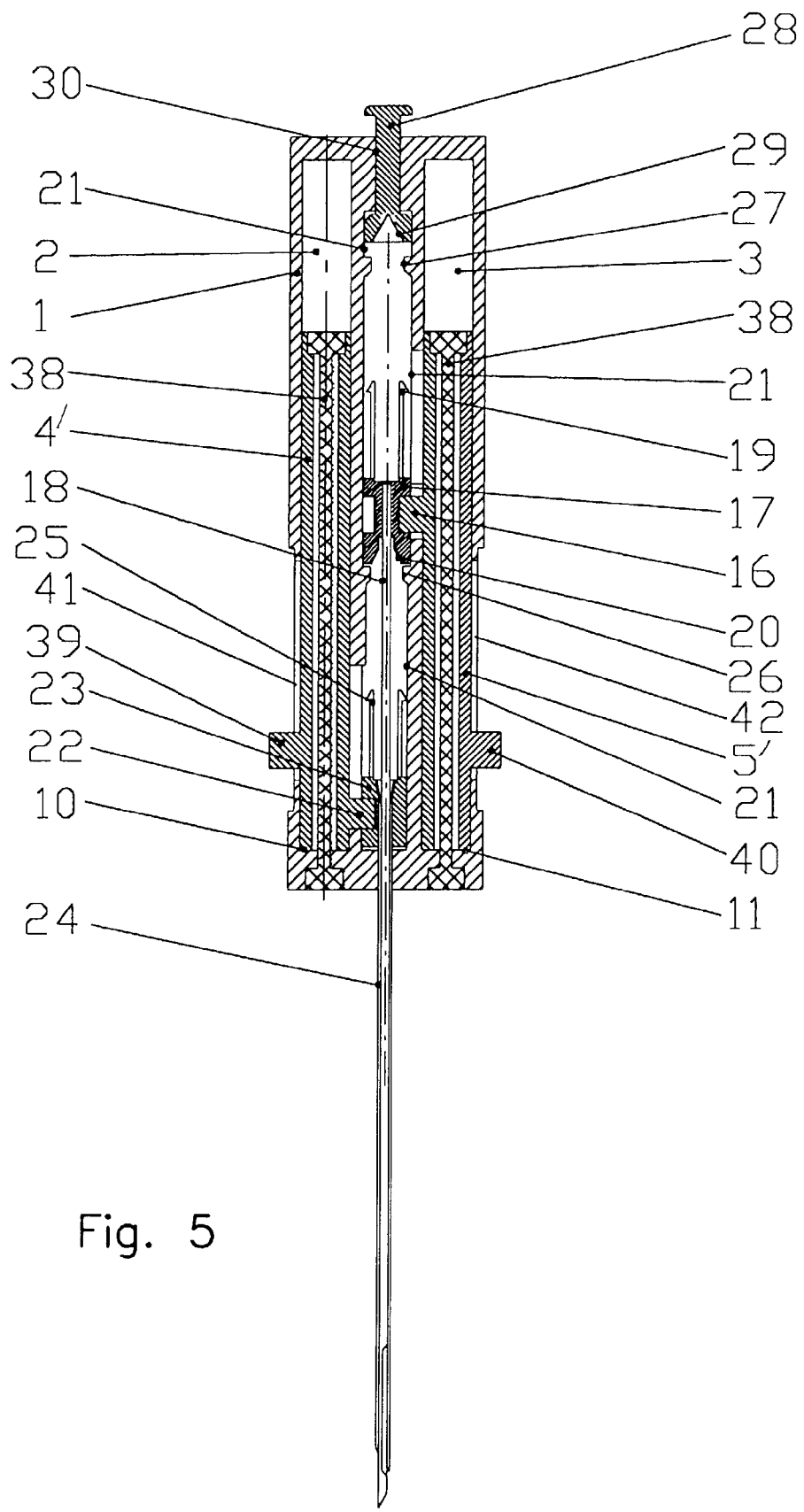
FIG. 5 is a sectional view of a third embodiment using two rubber tension springs as spring force storage structures.

FIG. 5 shows a biopsy device in a third embodiment in a rest position, that is with the springs relaxed. In contrast to the two embodiments described above, each of the spring storage devices includes at least one highly elastic rubber tension spring 38 each being pre-tensioned already in the rest position. The rubber springs 38 extend axially through bores in the pistons 4 and 5 and have at their opposite ends head portions by which they are supported, at one end in the housing 1 near the seals 10 and 11 and, at the opposite end, they are fixed to the pistons 4 and 5. In this embodiment, the caps are not present by way of which the springs are tensioned like in the first two embodiments. Rather, the pistons 4' and 5' are each provided with operating handles 39 and 40 which extend from the housing 1 through guide slots 41 and 42.

As spring force storage elements highly elastic bands, preferably rubber bands, are suitable which rubber bands are guided outside the housing and are attached thereto. They may act on carrier members, which transfer their movement to the biopsy needle and the cannula within the housing. The carrier members may be guided together with a slide member parallel to the advance movement path of the biopsy needle and the cannula. Like in the earlier described embodiments, the movement is transferred to the coupling members of the biopsy needle and the cannula by projections, which extend into openings in the coupling members (see reference numerals 16 and 22 in the figures). Functionally, the slide members replace the pistons 4 and 5 of the embodiments described earlier. This particular variant is not shown in the drawings.

In all the embodiments described the biopsy needle 18 and the cannula 24 form, together with the coupling members 17 and 23, a separate design unit. This unit may be in the biopsy device a one-way unit, which is easily replaceable. If the replacement of this unit is required, the housing 1 of the biopsy device should be so designed that the central bore 21 is accessible for the replacement. Below, on the basis of FIGS. 6 and 7, two design concepts are presented. In these embodiments, rubber springs are shown but any of the spring arrangements referred to earlier may be used instead.

FIGS. 6a to 6c show an opening mechanism for the central bore 21 in top and side views, wherein the housing 1 includes the spring force storage devices 43 and is provided with a door 44. The door 44 is supported so as to be pivotable about the center part of one of the two spring force storage structures 43 and are provided with a snap lock structures 43 and is provided with a swap lock 45 for locking engagement with the other spring force storage structure. FIGS. 6a and 6b show the biopsy device closed, FIGS. 6c to 6e show it with the door 44 open, whereby the central bore 21 is accessible from the side. As apparent from FIGS. 6b and 6c, it is not necessary to open the side of the housing 1 remote from the biopsy needle for the insertion of the replaceable unit described above.

In this way, this area of the housing is not weakened so that the opening mechanism as described may also be used for a biopsy device according to the first embodiment with pressure medium-based spring force storage structures as shown in FIGS. 1 to 3, in which particularly this area of the housing 1 is stressed by the pressure of the pressure medium 9.

Figure 7A:
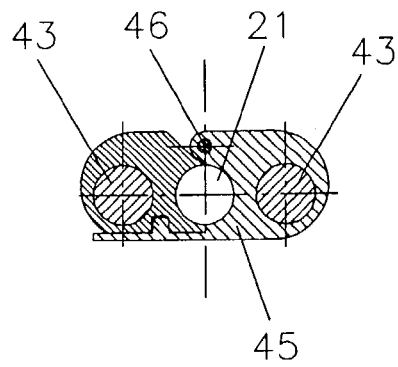
FIGS. 7a to 7d show another opening structure for device shown in FIG. 5.
Figure 7C:
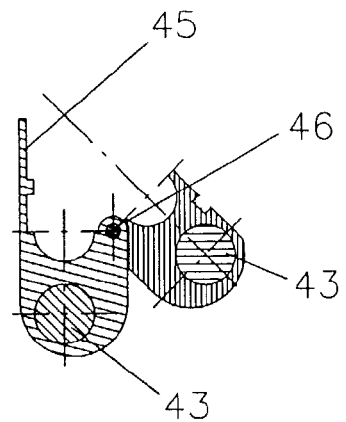
Figure 7B:
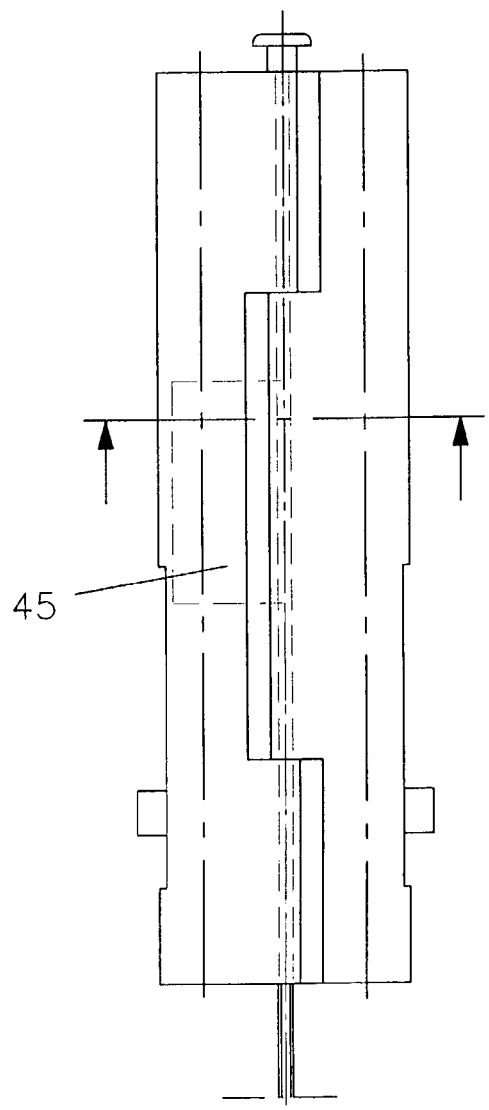
Figure 7D:
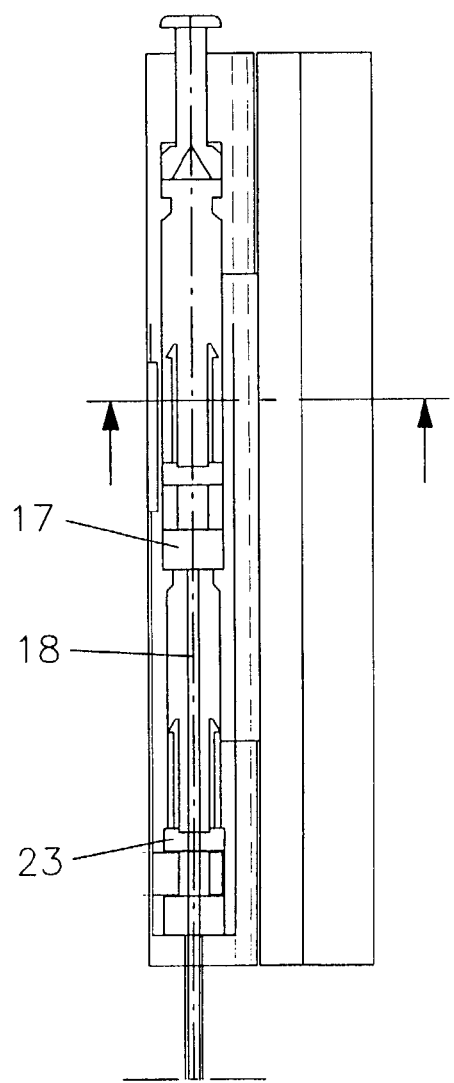

As an alternative, also the second variant of the opening mechanism is suitable wherein, as shown in FIGS. 7a to 7d, the housing 1 is divided along the central bore 21 such that two housing halves each with one spring force storage element are formed. FIGS. 7a and 7b show such a biopsy device in a closed state, FIGS. 7c and 7d show it opened. As apparent from the sectional views 7a and 7c, the two housing halves are pivotally joined by a hinge 46. When closed (FIG. 7a), a snap lock 45 of one housing half engages the other housing half. As a further variant, the hinge 46 may be replaced by a flexible element or by another snap lock.

It is pointed out that the biopsy needle and the cannula and also the spring force storage structure should not comprise any magnetic or electrically conductive material. Rather, they may consist of plastic, which may be fiber reinforced or they may consist of a ceramic material.

What is claimed is:

1. An automatic biopsy device for the removal of a soft tissue sample from a living organism, comprising:
    a) a housing
    b) a biopsy needle connected to a needle coupling member axially movably supported in said housing, said biopsy needle including at one side thereof near its tip a recess for receiving tissue,
    c) a cannula extending around said needle over part of its length connected to a cannula coupling member being axially movably supported in said housing,
    d) a first spring force storage structure arranged in said housing and operatively connected to said needle coupling member for biasing said needle toward an extended position,
    e) a first releasable locking means for locking said needle coupling member in a retracted position of said needle against the force of said first spring force storage structure,
    f) a second spring force storage structure arranged in said housing and operatively connected to said cannula coupling member for biasing said cannula toward an extended position,
    g) a second releasable locking means for locking said cannula coupling member in a retracted position against the force of said second spring force storage structure, each of said coupling members being movably supported in said housing,
    h) means for manually releasing said first locking means to permit said needle to be rapidly propelled with said needle coupling member by said first spring force storage structure, and
    i) means on said needle coupling member for releasing said second releasable locking means when said needle reaches an extended end position so as to permit said cannula to be rapidly propelled by said second spring force storage structure while moving over said needle and sever and retain any tissue contained in said recess of said needle, said biopsy needle and said cannula consisting of a non-magnetic and electrically non-conductive material for use of said device in connection with a magnetic resonance tomograph (MRT) and also said spring force storage structures consisting of a non-magnetic and electrically non-conductive material, said spring force storage structures comprising each a piston movably disposed in a cylinder including a compressible fluid for providing said spring force, and said pistons being hollow and having an opening at their front end for increasing the compressible fluid space.

2. An automatic biopsy device according to claim 1, wherein said biopsy needle and said cannula each are supported in an aligned fashion such that they are jointly insertable into, and removable from, said biopsy device.

* * * * *